United States Patent
Shimada et al.

(10) Patent No.: US 7,054,756 B2
(45) Date of Patent: May 30, 2006

(54) BACTERIOLOGICAL EXAMINATION SYSTEM

(75) Inventors: Kazuyuki Shimada, Kawaguchi (JP);
Hitoshi Matsuo, Musashino (JP);
Satoshi Mitsuyama, Tokyo (JP);
Hitoshi Otake, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 127 days.

(21) Appl. No.: 10/013,527

(22) Filed: Dec. 13, 2001

(65) Prior Publication Data

US 2002/0164676 A1    Nov. 7, 2002

(30) Foreign Application Priority Data

Apr. 3, 2001    (JP) .............................. 2001-104087

(51) Int. Cl.
*G01N 33/48* (2006.01)
*G01N 31/00* (2006.01)
*G06G 7/48* (2006.01)
*G06G 7/58* (2006.01)

(52) U.S. Cl. ........................... 702/19; 702/19; 702/22; 703/11; 703/12

(58) Field of Classification Search ................ 702/19, 702/22
See application file for complete search history.

(56) References Cited

FOREIGN PATENT DOCUMENTS

JP    04-346779    5/1991

OTHER PUBLICATIONS

The American Heritage Dictionary Second College Edition, 1982, p. 1041.*
Print out of http://www.cdc.gov/mmwr/wk/mm4529.pdf, Mar. 16, 2005, 1 page.*
"Cases of Selected Notifiable Diseases, United States, weeks ending Jul. 20, 1996, and Jul. 22, 1995 (29th Week)", MMWR, Jul. 26, 1996, http://www.cdc.gov/mmwr/PDF/wk/mm4529.pdf, p. 642.

* cited by examiner

*Primary Examiner*—John Brusca
*Assistant Examiner*—Russell S. Negin
(74) *Attorney, Agent, or Firm*—Reed Smith LLP; Stanley P. Fisher, Esq.; Juan Carlos A. Marquez, Esq.

(57) ABSTRACT

In a bacteriological examination system, an expected range of drug sensitivity is calculated from the results of statistics of data acquired at past drug sensitivity tests. Testing panels accommodating drugs of different densities (ex. increasing by increments) covers the calculated expected range are selected for testing. An average-per-sample value of drug sensitivities of bacteria that reside in a hospital and an average-per-sample value of drug sensitivities of bacteria that reside in a limited region are preserved separately in a results-of-test database. A difference between statistical values of drug sensitivities of one bacterial species in a bacterial classification group residing in a hospital to an object drug and statistical values of drug sensitivities of the bacterial species residing in a limited region is calculated. The difference then is divided by the average-per-same value in the limited region. An average-per-bacterial species value is then obtained by averaging the difference-division values of the involved species to obtain a drug fastness index relative to the object drug.

4 Claims, 6 Drawing Sheets

DRUG SENSITIVE STATISTICS DATABASE EXTRACTION KNOWLEDGEBASE — 115

| CONDITIONS/DB | INDIVIDUAL | IN-HOSPITAL | REGIONAL | NATIONAL | SPECIAL ··· |
|---|---|---|---|---|---|
| NEW PATIENT & REGIONAL | — | — | ○ | — | — |
| OTHER DISTRICT | — | — | — | ○ | — |
| HAVE EXPERIENCE IN GOING ABROAD | — | — | — | — | ○ |
| PATIENT WHO CAME THE HOSPITAL BEFORE | ○ | — | — | — | — |
| INFECTED OTHER BACTERIA | — | — | ○ | — | — |
| INPATIENT | ○ | — | — | — | — |
| IN-HOSPITAL INFECTION | — | ○ | — | — | — |
| ⋮ | | | | | |
| ENVIRONMENT EXAMINATION | — | ○ | — | — | — |

|  | UNIT PRICE | ABPC | CCL ... |
|---|---|---|---|
| A-02 | ¥500 | 8-16 | 4-16 |
| A-01 | ¥800 | 2-16 | 2-16 |
| ... | | | |
| EXPECTED RANGE | | 8.3-10.7 | 5.4-8.2 |
| DRUG FASTNESS INDEX | | 1.75 | 0.33 |

FIG. 7

OUTPUT OF EXAMINATION RESULT

START
↓
OBTAIN EXAMINATION RESULT — 1301
↓
CALCULATE DRUG FASTNESS INDEX — 1302
↓
CHANGE PRESENTATION ORDER OF DRUGS — 1303
↓
OUTPUT EXAMINATION RESULT — 1304
↓
END

FIG. 8

EXAMINATION RESULT — 1501

BACTERIA NAME
　SA
DRUG SENSITIVE

| | DRUG | SENSITIVE | STRENGTH | FASTNESS INDEX |
|---|------|-----------|----------|----------------|
| 1 | CCL | 8 | A | 0.33 |
| 2 | ABPC | 8 | A | 1.75 |
| 3 | : | | | |

BACTERIOLOGICAL EXAMINATION SYSTEM

BACKGROUND OF THE INVENTION

1. Field of the Invention

The present invention relates to a bacteriological examination system and an information system for use in medical institutions.

2. Description of the Related Art

In recent years, storage of resources outside a testing room or adoption of a facility management service ("FMS") has been promoted. For a testing room within a hospital, there is an urge demand for reducing testing costs and improving the status of staff members. As for a bacteria testing room, staff members are demanded not only to reduce the testing costs but also to prevent a drug-fast bacterial species, that has become an object of public concern these days, from generating.

It is a technician's job to identify a bacterial species having infected a patient via a sample of the patient. The technician then reports the test result together with the name of the bacterial species, an antibacterial agent (drug) which is destructive to the identified bacterial species, and the drug sensitivity of the bacterial species to the drug. The drug sensitivity is the minimum concentration of the drug with which the growth of the bacterial species is inhibited and it is used to express the efficacy of the drug.

A bacteriological examination system is a system for testing the drug sensitivities of a bacterial species. In the bacteriological examination system, a panel having a plurality of wells juxtaposed in rows and columns is used to perform a drug sensitivity test on one bacterial species with respect to a plurality of drugs. The same drug is poured into one row of wells in the panel with various densities. A bacterial species can be tested for the drug sensitivities to a plurality of drugs at one time. The technician selects a panel to be used for a drug sensitivity test from different kinds of panels.

For example, the bacteriological examination system described in the Japanese patent publication 04-346779 uses a plate that corresponds to one row of the foregoing panel. Different drugs are combined to test a bacterial species for the respective drug sensitivities, and the results of the test are provided.

Drug-fast bacteria are bacteria whose drug sensitivities to a specific drug are equal to or lower (i.e., their minimum drug concentrations are higher) than a certain value. It is known that MRSA is fast to mesitylene and VRE is fast to vancomycin.

One of the factors that generates the drug-fast bacteria is that a physician administers the same drug repeatedly because the efficacy of the drug against bacteria is therapeutically high. Consequently, the sensitivity of the bacteria to the drug is gradually lowered. Eventually, the bacteria becomes fast to the drug. Physicians must therefore administer another drug while taking account of the fastness of a bacterial species to the drug.

In the aforesaid two bacteriological examination systems of the related arts, a technician must select drugs for performing a drug sensitivity test with respect to a bacterial species, and report the drug sensitivities of the bacterial species. For this reason, the technician may test the drug sensitivity of a bacterial species to a drug that is not actually used by a physician on a patient or the drug sensitivities of bacteria not residing in the hospital of interest. Moreover, in the two systems, the densities of drugs are fixed. A drug density which is so high as to seriously affect or poison a patient and a drug density which is so low that a bacterial species is apparently fast to the drug of the density thus insensitive to the drug. Thus, unused drugs or drugs with densities are too high or low are tested and wasted.

Moreover, when a physician administers a drug for a patient, the physician wants to review the drug sensitivities of bacteria residing in a hospital so as to suppress further generation of drug-fact bacteria. However, a bacteria testing technician does not provide information that may be used as a distinctive index of fastness of a bacterial species to a drug for the physician to review the fastness to the drug.

SUMMARY OF THE INVENTION

An object of the present invention is to provide a bacteriological examination system for decreasing the number of wasteful tests derived from selection of unnecessary drugs or diluted drugs to improper densities so as to reduce testing costs.

Another object of the present invention is to provide a bacteriological examination system capable of objectively presenting to physicians the degrees of latent fastness of bacteria residing in a hospital.

Other objects of the present invention will be apparent from the description of embodiments.

A typical feature of the present invention is implemented in a bacteriological examination system that comprises a sample information retrieving means, a testing panel database, a drug-sensitivity statistic database, and a testing panel extracting means. The sample information retrieving means acquires sample information concerning a to-be-tested sample for a bacterial species which includes information of an individual, such as a patient or an animal, from which the sample is extracted and the names of the bacterial species. The ranges of drug densities to be accommodated by each of a plurality of testing panels are recorded in the testing panel database. The statistical values of the drug sensitivities of each bacterial species to a plurality of drugs, which are obtained from past tests, are recorded in the drug-sensitivity statistic database. The testing panel extracting means calculates an expected range of drug sensitivity of the bacterial species in the objective sample according to the name of a bacterial species acquired by the sample information retrieving means and a statistical value retrieved from the drug-sensitivity statistic database. The testing panel extracting means selects testing panels from the testing panels recorded in the testing panel database based upon the expected range of drug sensitivity.

In particular, the drug-sensitivity statistic database includes an in-hospital drug sensitivity database and a regional drug sensitivity database. The statistics of the drug sensitivities of bacteria, which reside in the hospital, are recorded in the in-hospital drug sensitivity database. The statistics of the drug sensitivities of bacteria, which reside in a limited region, are recorded in the regional drug sensitivity database. In order to calculate the expected range of drug sensitivity of bacteria in the sample, one of the in-hospital drug sensitivity database and regional drug sensitivity database is used based on sample information.

Another feature of the present invention is implemented in a bacteriological examination system that calculates and presents the degree of latent fastness of a bacterial species to each drug as a drug fastness index. Such a cross-species index is based upon an underling assumption of a correlation among the drag resistance of the bacterial species so as to express a rising degree of drug resistance against one object drug in a hospital, which is rather indirect and latent than the traditional direct drug fastness/resistance concept. The degree of latent fastness of the bacterial species to one drug is objectively indicated in comparison with the degree of latent fastness to another drug. Specifically, the averages of the drug sensitivities of bacteria residing in the hospital, which are recorded in the in-hospital drug sensitivity database, and the averages of the drug sensitivities of bacteria residing in a limited region, which are recorded in the regional drug sensitivity database, are employed. A difference between the average of the drug sensitivities of each predetermined bacterial species from a plurality of samples residing in the hospital and the average of the drug sensitivities of the predetermined bacterial species from a plurality of samples residing in the limited region is calculated for each bacterial species. The difference then is divided by the regional average drug sensitivity to obtain a normalized value for each bacterial species. By adding the normalized values then dividing the adding result with the number of bacterial species, a drug fastness index relative to the object drug is obtained.

Another feature of the present invention will be apparent from the description of a preferred embodiment.

BRIEF DESCRIPTION OF THE DRAWINGS

FIG. 7 is a flowchart describing actions for presenting the results of a test;

FIG. 8 is a conceptual diagram showing an example of the test results presented by the bacteriological examination system in accordance with the embodiment in FIG. 1;

DESCRIPTION OF THE PREFERRED EMBODIMENTS

Figure 1:
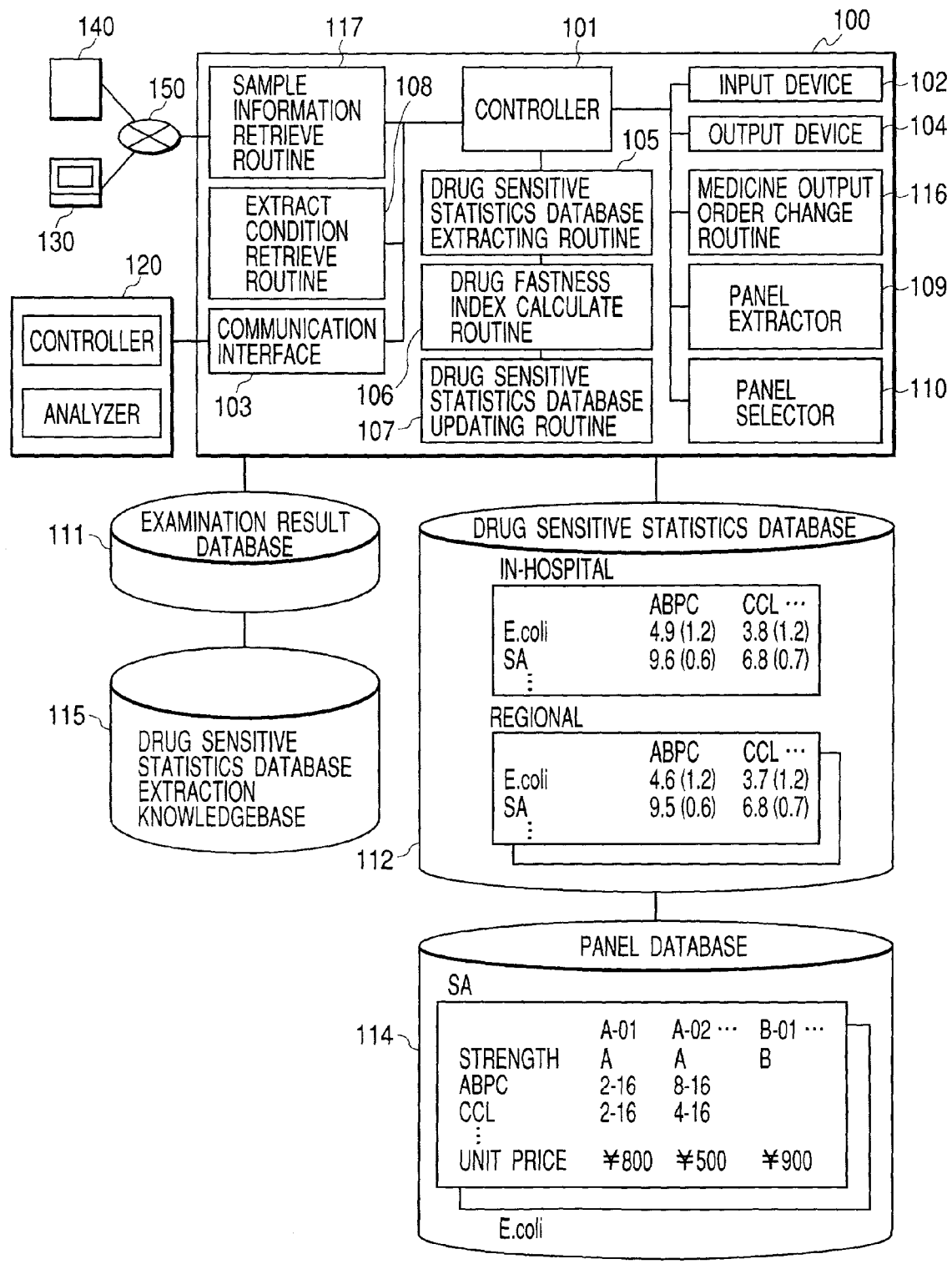
FIG. 1 is a block diagram of a bacteriological examination system in accordance with a preferred embodiment of the present invention.

FIG. 1 shows the configuration of a bacteriological examination system 100 in accordance with a preferred embodiment of the invention. The bacteriological examination system 100 comprises a controller 101, an input device 102, a communication interface 103, an output device 104, a drug sensitive statistics database extracting routine 105, a drug fastness index calculate routine 106, a drug sensitive statistics database updating routine 107, an extract condition retrieve routine 108, an panel extractor 109, a panel selector 110, an examination result database 111, a drug sensitive statistics database 112, a panel database 114, a drug sensitive statistics database extraction knowledge base 115, a medicine output order change routine 116, a sample information retrieve routine 117, and a bacterial tester 120.

The bacteriological examination system 100 communicates with an input/output terminal 130 over a network 150. Moreover, the bacteriological examination system 100 communicates with other bacteriological examination system 140 over the network.

The network 150 is supposed to be a network connected to the premises of a hospital but may be a regional network or a broad-area network.

In the drug sensitive statistics database 112, the averages of drug sensitivity tests performed on samples of patients who may be infected with bacteria within the hospital or the averages of the drug sensitivity tests performed on bacteria residing in the hospital (as part of environment tests) as well as the relevant standard deviations σ are recorded in an in-hospital average database. The samples can be extracted from one patient or many patients. Moreover, the averages of the drug sensitivity tests performed on samples of patients who may be infected with bacteria within the region where the hospital is located, or the averages of data acquired from the drug sensitivity tests performed on samples which are reported by external organizations as well as the relevant standard deviations are recorded in a regional average database. Herein, the drug sensitivities of a sample of a patient who may be infected with a bacterial species in a region may be measured in a testing room within the hospital. Alternatively, an average of the drug sensitivities of a bacterial species with which a patient is infected may be recorded in a personal average database, or an average of the drug sensitivities of the bacterial species that resides over a nation may be recorded in a national average database. An average of the drug sensitivities of a specific bacterial species such as malaria may be recorded in a special average database.

The input device 102 is a touch panel, a keyboard, or a mouse. Moreover, the output device 104 is a CRT, or a printer.

Figure 2:
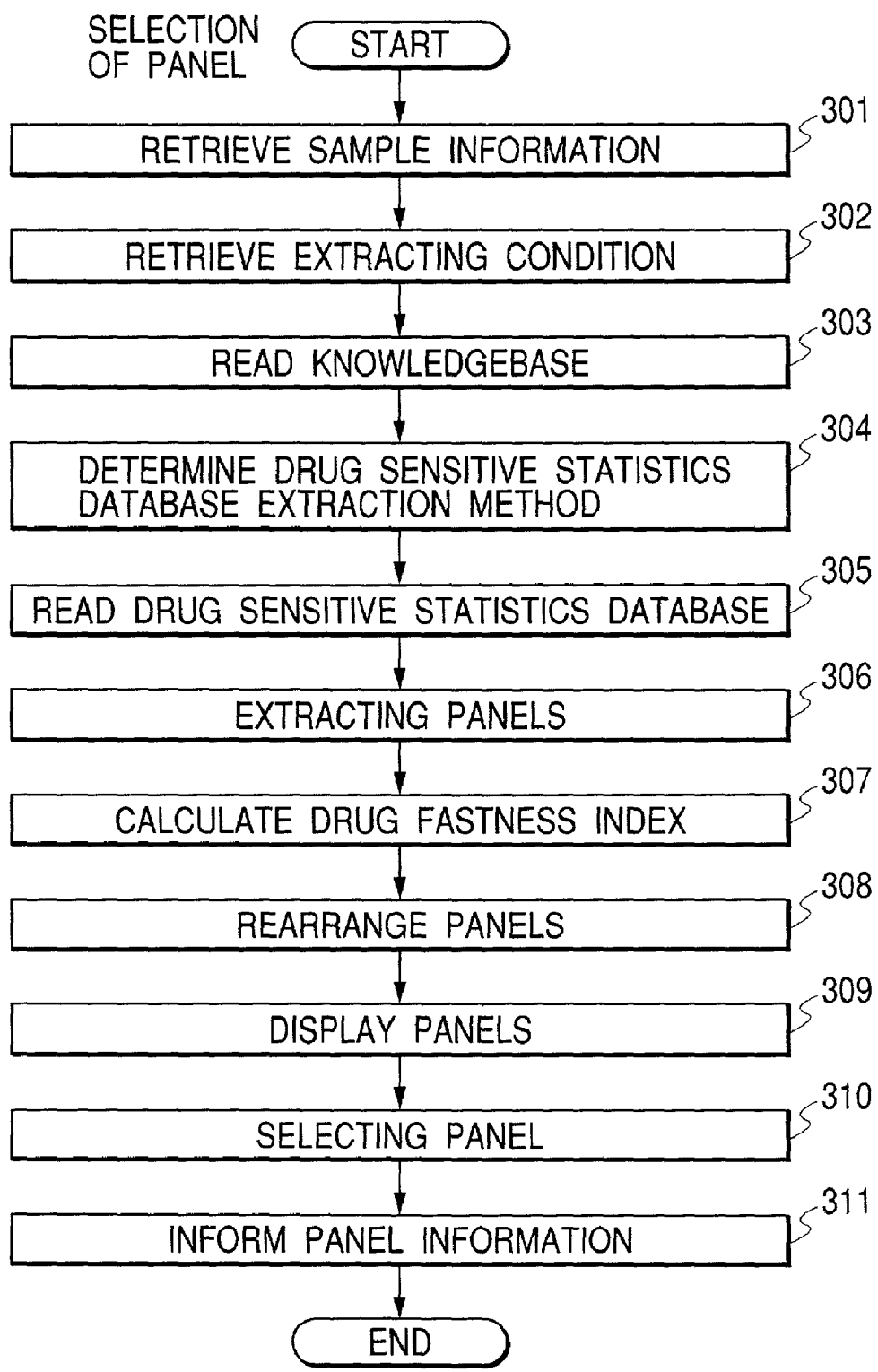
FIG. 2 is a flowchart describing actions to be performed for selecting a panel of the embodiment in FIG. 1.

FIG. 2 is a flowchart describing actions performed in the bacteriological examination system 100 when a technician selects a panel. First, the bacteriological examination system is started up. At a sample information retrieving step 301, the controller 101 activates the sample information retrieve routine 117 so as to acquire input sample information which a physician has entered at the input/output terminal 130.

The sample information includes clinical information concerning a patient whose sample is collected, and oral consultation information. The clinical information includes a date of an initial consultation, dates of second and subsequent consultations, and a date of hospitalization, and the oral consultation information includes a history of overseas trips. The sample information also includes the name of a bacterial species detected in a sample. Moreover, the sample information includes information concerning an environment test, a test to be performed when a patient is doubted to be infected with a bacterial species within a hospital, or the management of infectious diseases. The name of a bacterial classification group may be an academic name, such as *Staphylococcus aureus,* or a generic name, such as Gram-positive bacteria.

A technician may enter the sample information at the input device 102 on behalf of a physician.

At a step 302, the controller 101 activates an extract condition retrieve routine 108 so as to acquire the conditions for extraction which a physician has entered with the input/output terminal.

The conditions for extraction include the strength of a drug, whether the cost of testing is taken into consideration, and whether the fastness of a bacterial species relative to a drug is taken into consideration.

At step 303, the controller 101 reads the drug sensitive statistics database extraction knowledge base 115.

At step 304, the controller 101 selects a drug-sensitivity statistic database by referencing the drug sensitive statistics database extraction knowledge base 115 with the sample information acquired at the sample information retrieving step 301.

Figures 3, 4:
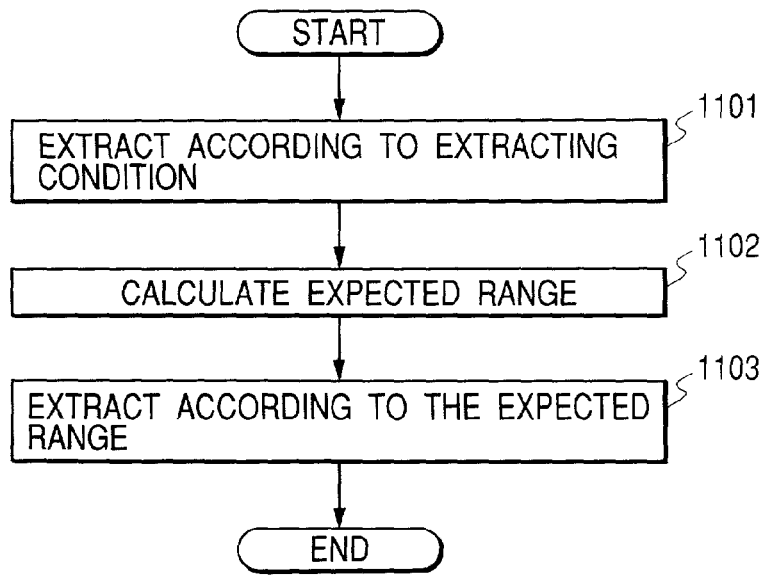
FIG. 3 is a conceptual diagram showing an example of a drug sensitive statistics database extraction knowledge base.
FIG. 4 is a flowchart describing actions for selecting a panel.

FIG. 3 shows an example of the drug sensitive statistics database extraction knowledge base 115. The illustrated example demonstrates that when a patient whose sample is collected has consulted the physician for the first time and lives at an address in the same region as the region in which the hospital is located, the controller 101 adopts the regional average database as the drug-sensitivity statistic database. When a patient has consulted the physician for the first time and lives at an address in a region different from the region in which the hospital is located, the national average database is adopted. When a patient has consulted the physician for the second or subsequent time or is an inpatient, the drug sensitivities of a bacterial species, with which the patient is infected, may have to be managed under the name of the patient. In this case, the personal average database is adopted. On the other hand, a drug sensitivity test may be performed on a bacterial species in a sample of a patient who is highly doubted to be infected with the bacterial species within the hospital, or a drug sensitivity test may be performed on a bacterial species in a sample of a patient as part of an environment test to be performed on the environment in the hospital. In this case, the drug sensitive statistics database extraction knowledge base 115 indicates that the in-hospital average database should be adopted as the drug-sensitivity statistic database.

At step 305, the controller 101 reads the drug-sensitivity statistic database according to the result of step 304.

At step 306, the controller 101 activates the panel extractor 109 so as to select panels by referencing the panel database using the name of the bacterial species or the effectiveness of a drug.

FIG. 4 describes actions to be performed at step 306 for selecting a panel. First, at step 1101, a panel is selected according to the name of the bacterial species and the strength of a drug which are acquired at step 302. A panel to be used for drug sensitivity tests for a bacterial species has a number of wells. A drug whose density is varied by increments within a range are poured into the rows of wells in order to measure a minimum density with which the drug hinders the growth of the bacterial species, whereby the bacterial species is incubated and tested for drug sensitivities thereof The strength of a drug in a panel signifies the strength of the drug of a maximum density among the incremental densities. Assuming that the strength of a drug is the same, for example, A, a panel A-01 covers the densities of ABPC within a range from 2 to 16, and the densities of CCL within a range from 2 to 16. A panel A-02 covers the densities of ABPC within a range from 8 to 16, and the densities of CCL within a range from 4 to 16. Thus, a plurality of kinds of panels is prepared in association with different ranges of densities of drugs, and any test ranges of the panels are adjustable. At step 1101 in FIG. 4, a plurality of panels are selected as candidates to be adopted for tests based on the designated name of a bacterial species and the strength of drugs. Next, at step 1102, an expected range of drug sensitivity of the bacterial species to each drug is calculated by referencing the drug-sensitivity statistic database that is read at step 304. Preferably, the expected range of drug sensitivity is determined to the range from {(average value)−2σ} to {(average value)+2σ}. The drug sensitivity of the objective bacteria sample should be in the expected range in a probability of 95%. When the drug sensitive statistics database 112 is referenced, the expected range of drug sensitivity of the bacterial species to ABPC is from 8.3 to 10.7 and the expected range of drug sensitivity of the bacterial species to CCL is from 5.4 to 8.2. Alternatively, the coefficient to the standard deviation σ in the above formula can be varied from '2' according to a desired probability that the drug sensitivity of bacteria in the objective sample falls within the expected range of drug sensitivity.

Thereafter, at step 1103, a plurality of panels are selected based on the calculated expected ranges of drug sensitivities relative to respective drugs such that each of drug density ranges accommodated by each of the selected panels covers the corresponding expected range of drug sensitivity.

Referring back to FIG. 2, the controller 101 activates a drug fastness index calculate routine 106 so as to calculate a drug fastness index.

Figures 5, 6:
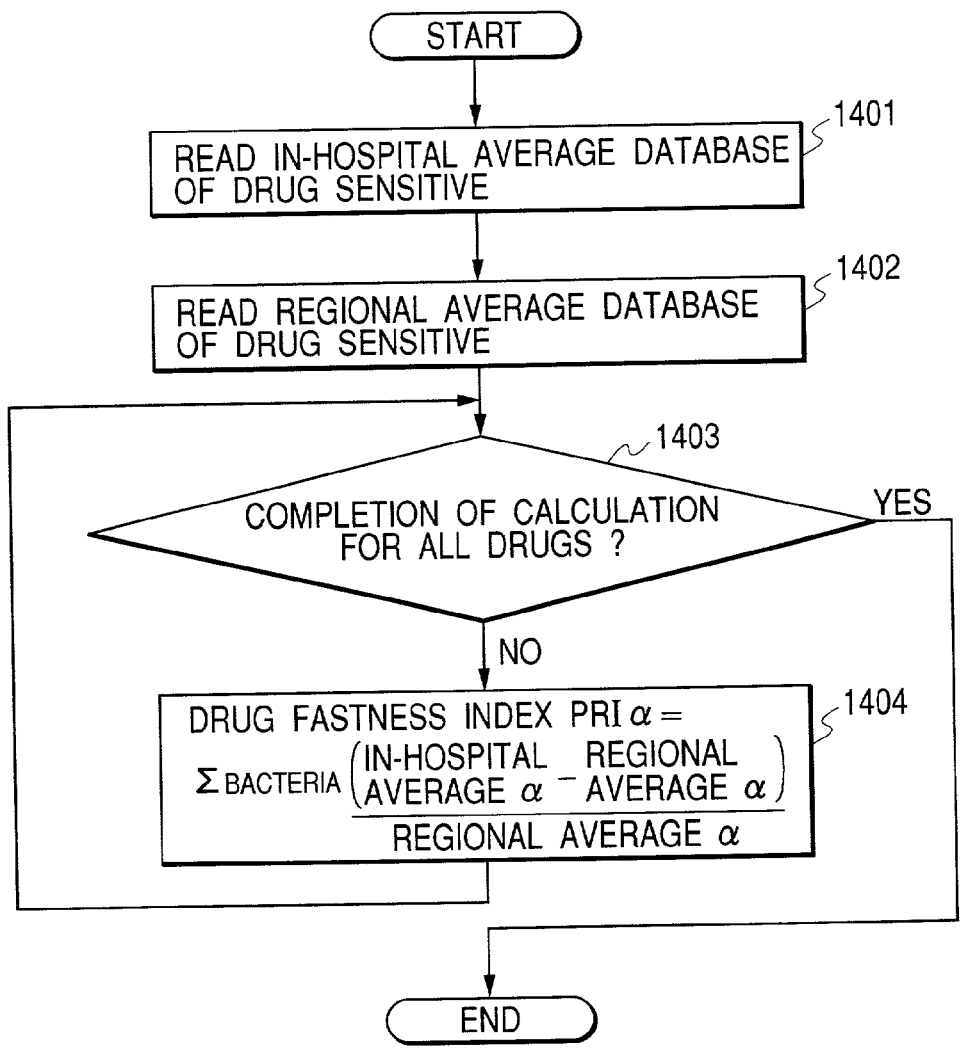
FIG. 5 is a flowchart describing actions for calculating a drug fastness index.
FIG. 6 shows a screen image of a presentation of the bacteriological examination system of the invention.

FIG. 5 shows a flowchart describing the drug fastness index calculate routine 206. First, at step 1401, the in-hospital drug-sensitivity statistic database is read. At step 1402, the regional drug-sensitivity statistic database is read. It is judged at step 1403 whether all of drug fastness indexes are calculated relative to drugs of interest. If it is judged as "No" at step 1403, the calculation of a drug fastness index relative to a next drug of interest is performed at step 1404.

A drug fastness index relative to a drug of interest is an index that objectively indicates in comparison with another drug whether one or a number of bacterial species are fast to the drug of interest for selecting a drug to be administered to cure an infectious disease. Specifically, a plurality of residential bacterial species, i.e., a largest possible number of residential bacterial species are designated in advance. A percentage by which an average of the drug sensitivities of each of the designated bacterial species that reside in a hospital is higher than an average of the drug sensitivities of each of the designated bacterial species that reside in a limited region is calculated. The calculated percentages by each of which the average of the drug sensitivities of each of the bacteria that reside in the hospital is higher are simply averaged and adopted as the drug fastness index.

Assume that an average-per-sample of the drug sensitivities of a certain bacterial species x, which resides in a hospital, to the different densities of a certain drug α shall be an in-hospital average αx, and an average of the drug sensitivities of the same bacterial species x, which resides in a limited region, to the different densities of the drug α shall be a regional average αx. A drug fastness index PRIα is calculated according to the expression below.

$$PRI\alpha = \frac{1}{N} \sum_{X=1}^{N} \frac{\text{in-hospital average } \alpha x - \text{regional average } \alpha x}{\text{regional average } \alpha x},$$

where, N is a number of the bacterial species that are designated in advance.

Thus, a drug fastness index with respect to a drug of interest is calculated by averaging the normalized differences, each being derived from data of drug sensitivities for each bacterial species designated in advance. In the case where data of drug sensitivities for only one bacterial species are available, the averaging operation can be omitted. Namely, a normalized difference between an in-hospital average of drug sensitivity for one bacterial species and a regional average of drug sensitivity for the same one bacterial species is adopted as the drug fastness index.

Further, instead of species, higher levels of classification according to Bergey's Manual of Systematic Bacteriology, such as genus, family, section, etc., can be designated to calculate the drug fastness index.

The drug fastness index calculate routine 106 is terminated if it is judged at step 1403 in FIG. 5 that the calculation of drug fastness indexes relative to all of drugs of interest has been completed.

Thereafter, at step 308, the controller 101 re-sorts panels selected at step 306 according to the information acquired at step 302, that is, according to whether a testing cost is taken into consideration or the drug fastness is taken into consideration.

For example, when a testing cost is taken into consideration, the selected panels are re-sorted in ascending order of the testing cost When the drug fastness is taken into consideration, the lowest drug fastness index is preferred and selected from among the drug fastness indexes relative to the drugs accommodated by the panels according to the drug fastness indexes calculated at step 307. The panels are re-sorted in ascending order of the drug fastness index.

Thereafter, at step 310, the controller 101 presents the panels using the output device 104 with the panels held re-sorted at step 309.

FIG. 6 shows an example of a screen image 1200 presented by the bacteriological examination system 100 when the panels are re-sorted in ascending order of the testing cost at step 310. As seen from the screen image 1200, the panels selected at step 306 are re-sorted in ascending order of the testing cost.

Thereafter, at step 307, the controller 101 prompts selection of a panel for performing tests from among the panels presented at step 306. When technician who is using the bacteriological examination system selects a panel that ranks top, the technician can perform a required test and designate a panel with which the test can be achieved at the lowest testing cost.

Thereafter, at step 308, the controller 101 transfers the information of the panel selected at step 307 to the bacteria tester 120.

As mentioned above, the technician who is using the bacteriological examination system can select a panel that enables testing of a bacterial species using most economical drugs at optimal densities in response to a physician's request. Any unnecessary tests will not be performed, and the cost of testing is reduced.

FIG. 7 is a flowchart describing actions to be performed in the bacteriological examination system 100 in order to present the results of a test. First, the bacteriological examination system 100 starts up. The controller 101 receives the results of a test from the bacteria tester 120 at step 1301. The controller 101 then activates the drug fastness index calculate routine 106 so as to calculate a drug fastness index at step 1302. The controller 101 then activates the medicine output order change routine 116 so as to change the order according to which drugs are presented (step 1303). Herein, the drugs are re-sorted in ascending order of the drug fastness index calculated at step 1302. At step 1304, the controller 101 presents the test results as they are re-sorted by the medicine output order change routine 116. At step 1304, the test results are presented in writing. Alternatively, the test results are presented directly on the screen of the input/output terminal 130 as chosen by a physician. Alternatively, the test results may be transferred to a terminal of another physician connected via the network 150.

FIG. 8 shows an example of the results of a test 1501 presented at step 1304. Referring to FIG. 8, the results of drug sensitivity tests performed on a bacterial species with respect to drugs are presented while or after being re-sorted in ascending order of the drug fastness index.

A physician may reference the results of a test to determine whether a drug is to be administered to a patient. For example, referring to the test results shown in FIG. 8, the drug sensitivities of a bacterial species to ABPC and CCL are 8, and the strengths of ABPC and CCL are 1.37. The drug fastness index that is an index, of the latent fastness of the bacterial species to a drug, with respect to ABPC is 1.37, and the drug fastness index with respect to CCL is as low as 0.33. If the physician wants to prevent further generation of a drug-fast bacterial species, the physician would use CCL.

Consequently, a physician can objectively review the degree of latent fastness of a bacterial species to a drug that resides in a hospital, and therefore suppresses further generation of a drug-fast bacterial species.

Figure 9:
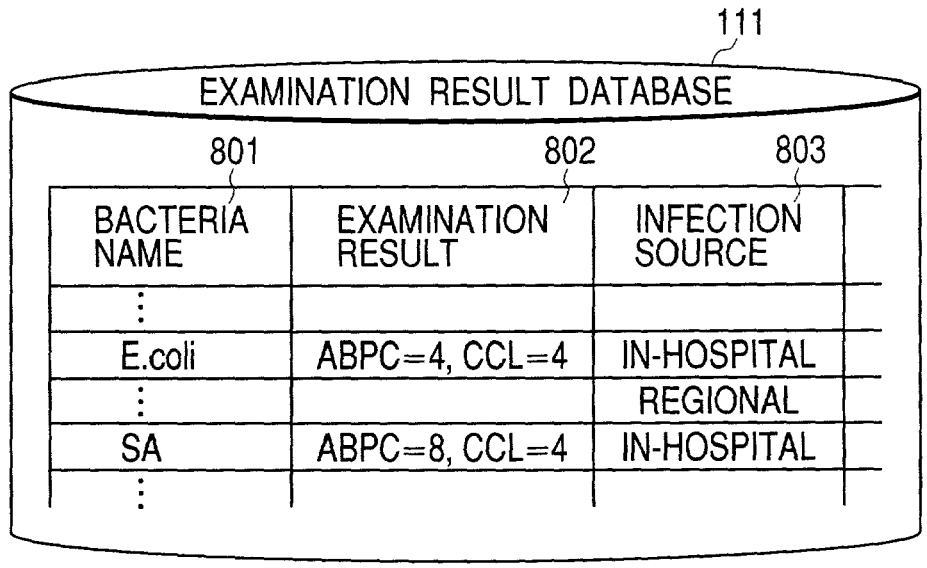
FIG. 9 is a conceptual diagram showing an embodiment of an examination result database.

FIG. 9 shows an example of the examination result database 111. The examination result database 111 consists of a field 801 in which the names of bacteria are recorded, a field 802 in which the test results are recorded, and a field 803 in which the places where patients are infected with the bacteria are recorded.

Figure 10:
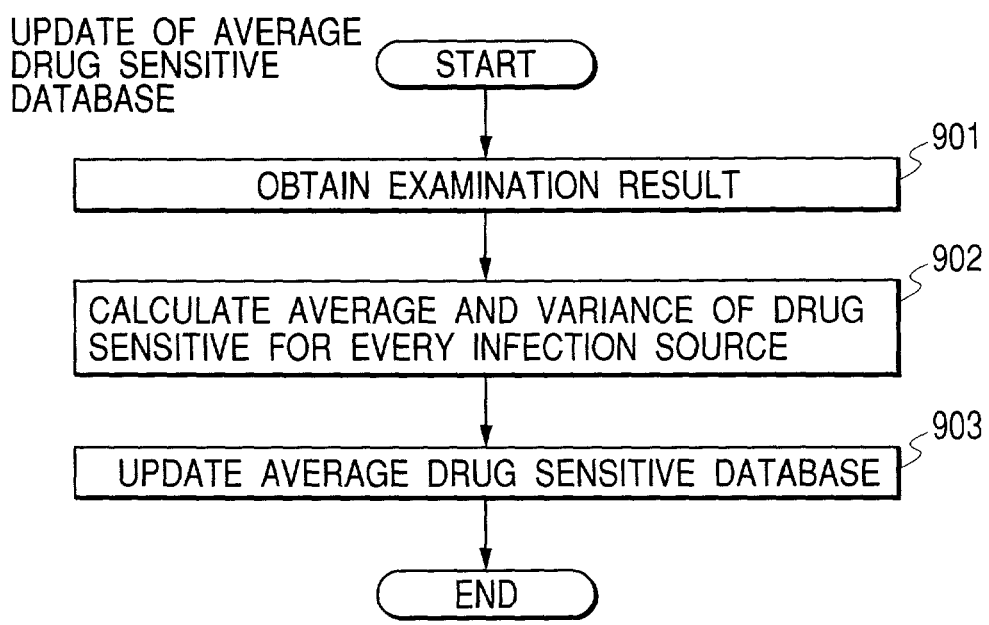
FIG. 10 is a flowchart describing actions for updating a drug sensitive statistics database.

FIG. 10 is a flowchart describing actions to be performed by the drug sensitive statistics database updating routine 107. First, the controller 101 activates the drug sensitive statistics database updating routine 107. The drug sensitive statistics database updating routine 107 retrieves the test results from the examination result database 111 at step 901. At step 902, the drug sensitive statistics database updating routine 107 calculates an average of drug sensitivities of each bacterial species and a standard deviation ("σ") thereof in relation to each infection source using the test results read at step 901. At step 903, the drug sensitive statistics database updating routine 107 updates the drug sensitive statistics database 1 12 with the average and variance calculated at step 902. The drug sensitive statistics database updating routine 107 is then terminated.

As mentioned above, the drug sensitive statistics database is updated if necessary. A technician who is using the bacteriological examination system can select an optimal panel more accurately.

One embodiment of the bacteriological examination system has been described so far. Alternatively, the present invention may be implemented in the bacteria tester 120.

Moreover, the description has been made under the assumption that each panel accommodates a plurality of drugs to be recorded in the panel database 114. Alternatively, a plate database in which each plate accommodates one drug is recorded. In this case, a technician who is using the bacteriological examination system 100 can select a plate for testing a bacterial species with respect to optimal drugs of optimal densities.

Moreover, the description has been made under the assumption that each panel accommodates a plurality of drugs to be recorded in the panel database 114. A drug database in which each drug is accommodated by one panel at a certain density may be recorded in the panel database 114. In this case, a technician who is using bacteriological examination system 100 can select optimal drugs of optimal densities.

Base upon the bacteria tester and bacteriological examination system described in relation to the embodiment, a technician who is using the bacteriological examination system can select a panel, which enables testing of a bacterial species with respect to optimal drugs of optimal densities, according to a physician's request. Consequently, any unnecessary test will not be performed such that testing costs are reduced.

Moreover, the drug sensitive statistics database can be updated if necessary. A technician who is using the bacteriological examination system can select an optimal panel more accurately.

Moreover, a physician can objectively review the degree of the latent fastness of a bacterial species with respect to each of drugs, that reside in a hospital, so as to suppress further generation of a drug-fast bacterial species.

What is claimed is:

1. A bacteriological examination system for measuring drug sensitivity of bacterial species, comprising:
    an in-hospital drug-sensitivity statistic database in which statistics of drug sensitivities of a plurality of bacterial species residing in a hospital towards a plurality of drugs are recorded;
    a regional drug-sensitivity statistic database in which statistics of drug sensitivities of the plurality of bacterial species residing in each region towards the plurality of drugs are recorded;
    a drug fastness index calculating routine for reading an average-per-sample drug sensitivity with respect to each bacterial species residing in hospital from said in-hospital drug-sensitivity database, for reading an average-per-sample drug sensitivity with respect to the same species of bacteria residing in a region from said regional drug-sensitivity database, for calculating a value by dividing difference between the in-hospital average-per-sample drug sensitivity of the bacterial species and the regional average-per-sample drug sensitivity of the bacterial species by the regional average-per-sample drug sensitivity of the bacterial species, and for averaging respective values of said each bacterial species so as to derive a drug fastness index with respect to the drug; and
    an output means for outputting the drug fastness index calculated by the drug fastness index calculating routine.

2. A method for bacteriological examination, comprising:
    providing an in-hospital drug-sensitivity statistic database in which statistics of drug sensitivities of a plurality of bacterial species residing in a hospital towards a plurality of drugs are recorded;
    providing a regional drug-sensitivity statistic database in which statistics of drug sensitivities of the plurality of bacterial species residing in a-each region towards the plurality of drugs are recorded;
    reading an average-per-sample drug sensitivity with respect to each bacterial species residing in hospital from said in-hospital drug-sensitivity database;
    reading an average-per-sample drug sensitivity with respect to the same species of bacteria residing in a region from said regional drug-sensitivity database;
    calculating a value by dividing the difference between the in-hospital average-per-sample drug sensitivity of the bacterial species and the regional average-per-sample drug sensitivity of the bacterial species by the regional average-per-sample drug sensitivity of the bacterial species; and
    averaging respective values of said each bacterial species so as to derive a drug fastness index with respect to the drug; and outputting the drug fastness index.

3. The bacteriological examination system according the claim 1, wherein said drug fastness index calculating routine calculates the drug fastness index for a plurality of drugs, and said output means outputs the drug fastness index in the order of their values.

4. The bacteriological examination system according the claim 2, wherein the drug fastness index is calculated for a plurality of drugs, and the drug fastness index is output in the order of their values.

* * * * *